United States Patent
Lopatin (10) Patent No.: US 8,242,477 B2
(45) Date of Patent: Aug. 14, 2012

(54) BRIGHT FIELD AND DARK FIELD CHANNELS, USED FOR AUTOMOTIVE GLASS INSPECTION SYSTEMS

(75) Inventor: Aleksey Lopatin, Toronto (CA)

(73) Assignee: Synergx Technologies Inc., Laval (CA)

( * ) Notice: Subject to any disclaimer, the term of this patent is extended or adjusted under 35 U.S.C. 154(b) by 423 days.

(21) Appl. No.: 12/523,005

(22) PCT Filed: Jan. 11, 2008

(86) PCT No.: PCT/CA2008/000057
§ 371 (c)(1),
(2), (4) Date: Nov. 14, 2009

(87) PCT Pub. No.: WO2008/083497
PCT Pub. Date: Jul. 17, 2008

(65) Prior Publication Data
US 2010/0051834 A1    Mar. 4, 2010

Related U.S. Application Data

(60) Provisional application No. 60/884,813, filed on Jan. 12, 2007.

(51) Int. Cl.
*G01N 21/86* (2006.01)

(52) U.S. Cl. .................. 250/559.4; 250/559.46

(58) Field of Classification Search .. 250/559.4–559.46; 356/239.1, 237.1–237.5, 239.7, 430
See application file for complete search history.

(56) References Cited

U.S. PATENT DOCUMENTS

| | | | |
|---|---|---|---|
| 6,437,357 B1 | 8/2002 | Weiss et al. | |
| 6,501,546 B1 | 12/2002 | Weiss | |
| 6,633,377 B1 | 10/2003 | Weiss | |
| 7,714,996 B2 * | 5/2010 | Yan et al. | 356/237.1 |
| 2007/0252996 A1 | 11/2007 | Rudert et al. | |

FOREIGN PATENT DOCUMENTS

| | | |
|---|---|---|
| CA | 2252308 | 4/2000 |
| CA | 2406624 | 11/2001 |
| CA | 2567061 | 12/2005 |
| JP | 2001235432 | 8/2001 |

* cited by examiner

*Primary Examiner* — Que T Le
(74) *Attorney, Agent, or Firm* — Bereskin & Parr LLP (57) ABSTRACT

An inspection system for inspecting a sheet of glass comprises an illumination module, a collimating lens system, a telecentric imaging lens system and a Time Delay Integration line-scan camera. The illumination module has a low coherence light source emitting light. The collimating lens system has a focal point on the main axis thereof on which focal point its light source is located. The collimating lens system produces a collimated sheet of light from the emitted light. This collimated sheet of light passes through the sheet of glass. The telecentric imaging lens system concentrates the sheet of light passed through the sheet of glass on an image formation plane.

20 Claims, 8 Drawing Sheets

BRIGHT FIELD AND DARK FIELD CHANNELS, USED FOR AUTOMOTIVE GLASS INSPECTION SYSTEMS

FIELD OF THE INVENTION

The present invention is related to the field of glass inspection systems. More particularly, the present invention is related to an automatic inspection system for the detection, identification and sizing of defects in curved or flat automotive sheets of glass.

BACKGROUND OF THE INVENTION

The automotive industry has quality standards that need to be respected when it comes to parts manufacturing. Because of high production rates, automating inspection of these manufactured parts is now necessary. Employing a number of physical principles, numerous efforts have been made through the years to develop systems that are suitable for the automated in-line inspection of automotive glass.

The requirement for simultaneous detection and identifying of a large variety of intrinsic float glass defects and manufacturing/processing defects has applied strong limitations on the design of inspection systems, narrowing down the choice of effective solutions suitable for the above-mentioned purpose.

Figure 1:
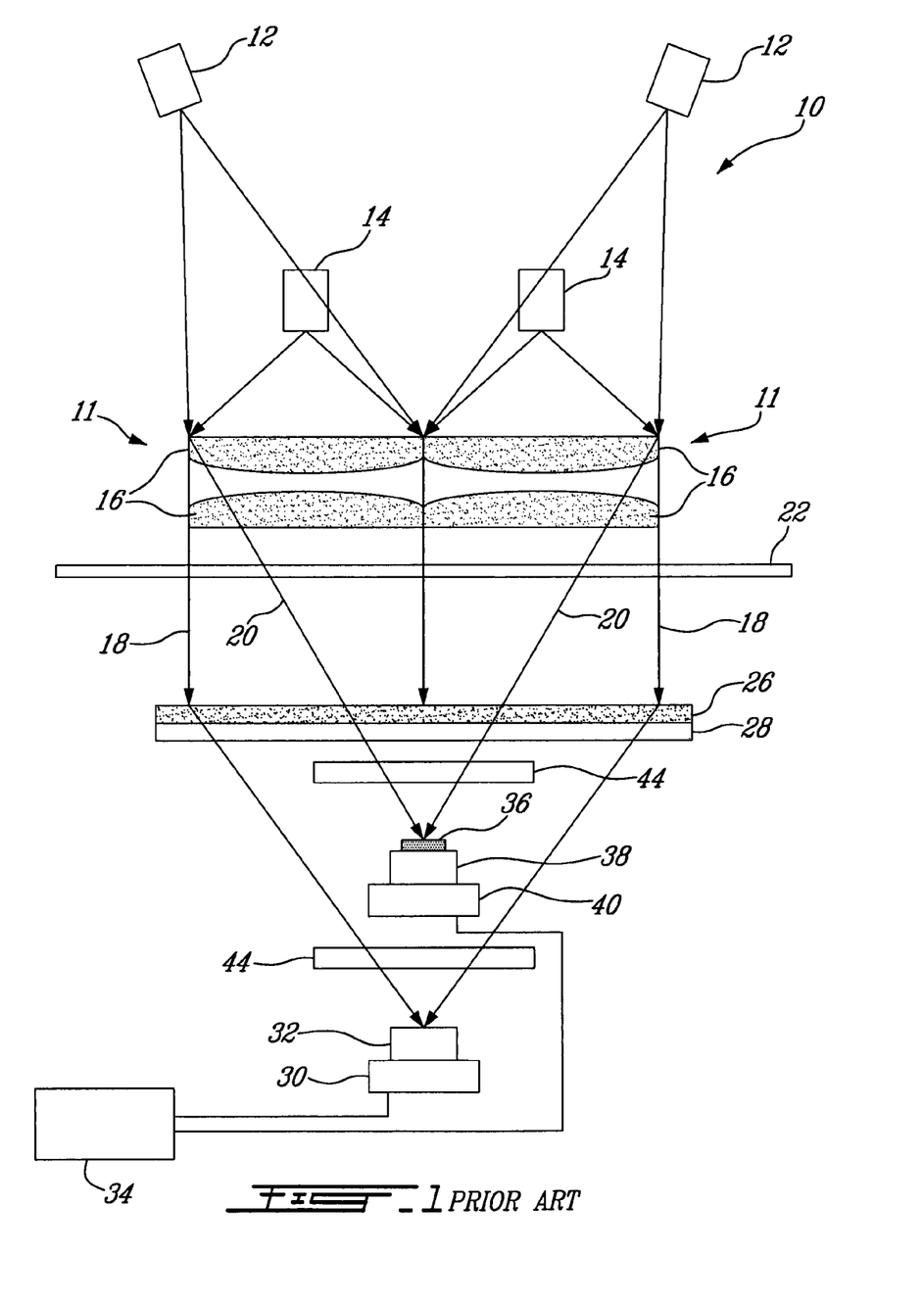
FIG. 1 is a schematic view of conventional Transmissive Bright Field/Dark Field channels of a flat glass inspection system of the prior art.

U.S. Pat. No. 6,437,357 to Weiss et al. is schematically detailed in FIG. 1 and represents the conventional implementation of a flat automotive glass inspection system 10, comprising transmissive directional coherent Bright Field (BF) and transmissive coherent Dark Field (DF) channels. As a matter of cost saving, both the BF and the DF channel illuminators are installed in a same compartment and employ the same collimating lens 11. Two identical DF laser modules 12 are used as light sources for the DF channel and two identical BF laser modules 14 are used as light sources for BF channel. The collimating lens 11 is made of two pairs of identical cylindrical lenses 16. Both BF laser modules 14 are installed at the respective focal points of both pairs of cylindrical lenses 16. As a result, divergent sheets of light, generated by BF laser modules 14 are converted into parallel, or collimated, BF sheets of light 18. Both DF laser modules 12 are installed in a symmetric way further away from the focal plane of both pairs of cylindrical lens 16. Consequently, divergent sheets of light, generated by DF laser modules 12 are converted into convergent DF sheets of light 20. In addition, DF laser modules 12 are slightly inclined relatively to the BF laser modules 14, so that there is a small angle between the emerging BF and DF sheets of light 18, 20. The BF sheets of light 18 and the DF sheets of light 20 pass through a flat glass sample 22, moving along a production conveyor. In FIG. 1, the conveyor would move the glass sample outwardly from the plane of FIG. 1.

The BF sheets of light 18 reach a semitransparent screen 26, attached onto the surface of a Fresnel lens 28. A BF camera 30 with attached BF objective lens 32 is focused onto the semitransparent screen 26. In the absence of defects, glass paintwork or grinded edge, a photosensitive element of the BF camera 30 is illuminated, hence the Bright Field channel name. Any significant departure from stationary illumination level is analyzed by an image acquisition/processing system 34 connected to the BF camera 30. Based on this analysis, the glass inspection system 10 generates a BF defect map for the inspected glass sample 22.

The converging DF sheets of light 20, propagating under an angle to the BF sheets of light 18, pass beside semitransparent screen 26 and Fresnel lens 28 to be absorbed by a spatial filter 36, attached to a DF objective lens 38. The DF objective lens 38 is attached to the DF camera 40. The spatial filter 36 absorbs direct DF sheets of lights 20. Therefore, the photosensitive element of the DF camera 40 is normally not illuminated, hence the Dark Field channel name. If the glass sample 22 has a defect that scatters or diffracts the DF sheets of lights 20 so that they pass beside the spatial filter 36, then they reach the DF objective lens 38, which focuses them onto the photosensitive element of the DF camera 40. Any significant departures from dark level are analyzed by the image acquisition/processing system 34, connected to the DF camera 40. Based on this analysis, the glass inspection system 10 generates the DF defect map for the inspected glass sample 22.

To decrease the dimensions of the glass inspection system 10 and to prevent broken glass drop onto expensive BF and DF objective lenses 32, 38, BF and DF sheets of lights 18, 20 are routed through fold mirrors 44.

U.S. Pat. No. 6,501,546 to Weiss describes an edge inspection module used to inspect the edge quality of flat automotive glass. Four of these modules generate collimated laser light beams, which propagate in the glass conveyor plane. The light beams illuminate the edges of the glass sample that moves along the conveyor. The module has its own built-in imaging system that acquires the light reflected/scattered by the ground edge of the glass. If the edge is free of defects, the intensity distribution of the scattered light across the edge is flat. Any significant departure from this flat intensity distribution is analyzed by an image acquisition/processing system connected to the edge inspection module. Based on this analysis, the glass inspection system generates the edge defect map for the inspected glass sample.

Long-term experience in exploiting both of these glass inspection systems has revealed several serious problems.

First, the use of lasers as light sources for the BF channels has shown that light intensity, passed through the glass samples, is modulated even in the absence of any glass defect. It manifests itself in a way that glass images, acquired with the BF channels, are disfigured with irregular strips of higher and lower light intensity. These intensity variations are known as "draw lines". This effect has been observed for all glass samples inspected so far, with all glass inspection systems built in correspondence with the conventional art described above. The most pronounced "draw lines" magnitude observed reached 14% of the stationary BF illumination level for clear glass samples with an average light transmissivity of 90-92%. This modulation of the BF light intensity effectively decreases the signal-to-noise ratio (SNR) and degrades the detection capability for a broad variety of defects.

In addition, multiple cases were reported where the glass inspection system falsely reported as defective clear glass samples because the intensity of the BF light inside the glass reached the light intensity outside the glass sample. This happened when the magnitude of the light modulation, combined with BF camera noise, reached or exceeded the intensity of the BF light outside the glass sample. In these cases the glass samples were rejected even though they were not defective.

After investigation, it was discovered that these false defect detections arise because laser light is coherent with a coherence length that is larger than the thickness of the inspected glass samples. As a result, the glass transmission coefficient for coherent light depends on the glass sample thickness even though there is no noticeable absorption inside the glass, such as with clear glass. As soon as the glass sample thickness changes by approximately 0.1 µm, the transmitted light intensity may experience a change of more than 10% depending on the laser coherence length, glass sample thickness, glass complex refractive index and laser light wavelength. Taking into account that the tolerance on automotive glass thickness is approximately 50 µm, the BF images of all glass samples were disfigured to a different extent because of the phenomenon described above.

The semitransparent screen 26 smoothes a strong light interference pattern which occurs when the collimated sheet of coherent light 18 passes through the Fresnel lens 28. However, the point spread function (PSF) width of the resulting BF channel ends up being at least twice as wide as the objective lens 32 PSF. This limits the capability of the BF channel to detect both small defects and defects with low optical density, thereby severely degrading the optical performance of the BF channel.

Furthermore, it has been shown that the combination into one housing of the BF channel, DF channel and edge modules is problematic. Indeed, the light generated by the edge modules and scattered by the glass sample edges, penetrates into the BF and DF cameras and creates overexposed BF and DF image fragments. These overexposed fragments usually are reported as large defects, and glass specimens are rejected even though they are defect-free. If the overexposed area is too large, the system fails to properly inspect it because of a lack of computer memory. In this case, defective glass samples pass the inspection as defect-free even though critical defects may really be present in the overexposed area.

Moreover, an attempt to cut the glass inspection system cost by combining collimating lenses for both the BF and DF channels has created another problem. It has been noticed that both the DF and BF channels have a blind zone in the center of the field of view because of both the imperfections at the junction of the collimating lenses and because of a difficulty with the alignment of the BF and DF beams. The blind zone width ranged from 0.6 to 1.5 mm out of typical 450 mm field of view. Defects traveling through this blind zone, or in close proximity to this zone, were not reported or were reported in a wrong way.

Additionally, the prior art DF channels proved to be incapable to inspect curved automotive glass products such as sidelights, windshields and backlights. It was discovered that, due to convergent the DF light sheet, a DF light source had to be positioned close to the inspected glass sample. Otherwise, the DF channel field of view rapidly decreased. Consequently, light scattering anomalies either inside or on the surface (such as dirt or dust) of the collimating lenses became visible. Light, scattered or diffracted by these anomalies, creates a spiky noise in the background of the DF camera, even in the absence of the inspected glass sample in the DF camera field of view. Although a background correction software algorithm was implemented to correct this problem, it still failed to solve the problem mostly because the scattered light refraction inside curved glass samples is unpredictable.

Glass inspection systems, built in accordance with the prior art, proved to be incapable to inspect dark tinted glass with a transmissivity down to 5% at a conveyor speed up to 800 mm/sec, which are typical automotive glass industry requirements nowadays. Light intensity reaching the cameras and cameras sensitivity proved to be insufficient to provide high-speed inspection for dark tinted glass.

Another problem arises with the inspection of automotive glass products that are partially coated with optically opaque paintwork on their surface. Nowadays, all finished windshields and backlights have such paintwork and final automotive glass inspection requires detecting defects above this paintwork.

The prior art glass inspection systems described above employ transmissive BF and DF techniques (TBF and TDF). These techniques are not adequate for automotive glass inspection above paintwork since light can not be transmitted through the paintwork.

In order to inspect curved automotive glass partially coated with paintwork, a Reflective Dark Field (RDF) inspection system was proposed by Rudert et al. in their PCT patent application published under the No. WO2005/116616. The glass inspection system proposed in this patent application is schematically described in FIG. 2.

Figure 2:
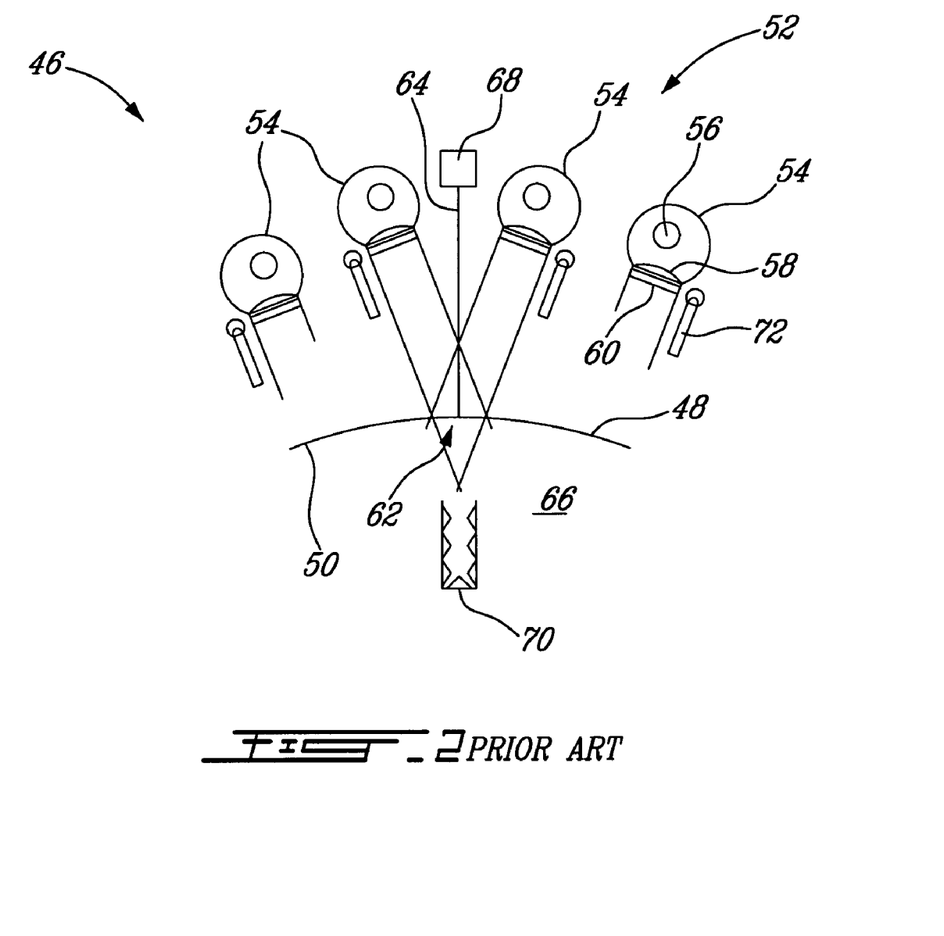
FIG. 2 is a schematic view of a Reflective Dark Field channel of an inspection system for curved and painted glass according to prior art.

Glass inspection system 46 was designed to detect scratches and scuff (abrasion) on a surface 48 of a glass sample such as a windshield 50. The glass inspection system 46 is equipped with an illumination unit 52, which comprises at least one light strip 54. Light, generated by lamps 56 and collimated by optics 58, passes through diffuser 60 and illuminates the surface 48 at an angle 62 relatively to the surface normal 64. A strip of light illuminates an area 66 on the windshield 50, which is imaged by a recording unit 68. A "light box" 70 is installed under the recording unit 68. Flaps 72 are used to shut down the light beams mechanically, because of the inertia of the lamps 56.

The main disadvantage of this system is that it is efficient only for defects with uniform angular scattering/diffraction characteristic. However, this is not the case for many defects like scratches satisfying to standard ASTM F-428-3, -4, -5 for example. During inspection, if the scratch happens to be oriented perpendicularly to the light strips orientation, the glass inspection system will miss them. On the contrary, scratches smaller than ASTM F-428-3 might be detected if their orientation during inspection is parallel to the light strips.

Therefore, there is a clear need for an improved glass inspection system.

SUMMARY OF THE INVENTION

It is an object of the present invention to provide a glass inspection system that overcomes or mitigates one or more disadvantages of known glass inspection systems, or at least provides a useful alternative.

In accordance with an embodiment of the present invention, there is provided an inspection system for inspecting a sheet of glass. The inspection system comprises an illumination module, a collimating lens system, a telecentric imaging lens system and a Time Delay Integration line-scan camera. The illumination module has a low coherence light source emitting light. The collimating lens system has a focal point on the main axis thereof on which focal point its light source is located. The collimating lens system produces a collimated sheet of light from the emitted light. This collimated sheet of light passes through the sheet of glass. The telecentric imaging lens system concentrates the sheet of light passed through the sheet of glass on an image formation plane. The Time Delay Integration line-scan camera is positioned in a general area of the image formation plane. The camera is equipped with an antiblooming device.

In accordance with another embodiment of the present invention, there is provided an inspection system for inspecting a sheet of glass. The inspection system comprises a camera and a peripheral RDF illumination module. The camera is positioned on and points toward a first side of the sheet of glass. The peripheral RDF illumination module surrounds the camera and is located on the first side, outside a field of view of the camera. The RDF illumination module is operative to illuminate the field of view with its RDF emitted light. The RDF illumination module is oriented so that the sheet of glass reflects the RDF emitted light away from the camera. The camera is positioned so as to be operative to receive the RDF emitted light if a RDF detectable defect is present on the sheet of glass and to avoid the RDF emitted light if no RDF detectable defect is present on the sheet of glass.

Optionally, this inspection system may be equipped with a TDF channel using a peripheral TDF illumination module. The TDF channel comprises a peripheral TDF illumination module, a collimating lens and a field lens. The peripheral TDF illumination module surrounds the camera and is located on a second side of the sheet of glass, outside the field of view of the camera. The TDF illumination module is operative to illuminate the field of view with its TDF emitted light. The camera is positioned so as to be operative to avoid said TDF emitted light if no TDF detectable defect is present in the sheet of glass and to receive the TDF emitted light if a TDF detectable defect is present in the sheet of glass. The collimating lens system is positioned between the TDF illuminating module and the sheet of glass. The collimating lens system is operative to direct the TDF emitted light away from said camera. The TDF illumination module is placed substantially within a focal plane of the collimating lens system. The field lens is positioned between the sheet of glass and the camera.

BRIEF DESCRIPTION OF DRAWINGS

These and other features of the present invention will become more apparent from the following description in which reference is made to the appended drawings wherein.

DETAILED DESCRIPTION OF THE INVENTION

Techniques for the manufacture of glass are known. For example, glass may be converted to a molten state and then cast onto molten tin metal so that glass with a smooth surface may be obtained. Nonetheless, the glass that has been cast may be subject to a number of defects, including the presence of bubbles, dirt, stones, tin-drip distortion and other defects. Some such defects might arise from raw materials fed to the process while other defects will arise from processing problems, including incorrect temperature or other process parameters and aging of apparatus, especially of kilns or other apparatus used in the heating of the glass.

Subsequent to the casting of the glass, the glass is cut into sheets and then transferred to a manufacturer of glass articles for a particular end use. In the automobile industry, for instance, the glass articles could be windows of a vehicle, in which event the manufacturer will shape the glass to a particular size and configuration, grind the glass edges, cut holes in the glass in locations as required, imprint logos or other writing in the glass and otherwise process the cut glass to a predetermined set of specifications. Despite care in operation of the process, the various steps can result in the formation of chips, cracks, scratches, and other defects that might render the glass unacceptable to a customer. The manufacturer must be able to detect the defects, and separate sheets of glass conforming to specification from those that do not.

Examples of some of the defects that may be present in a sheet of glass that is being prepared for use in, for instance, the automobile industry, include bubbles i.e. inclusion of gas in the glass in a generally spherical shape, blisters i.e. elongated bubbles, seeds i.e. minute bubbles, dirt, lint, shell chips i.e. small pieces of glass broken away from the main body of the glass, stones, strands i.e. very fine, string-like pieces of foreign matter embedded in the glass or laminates thereof, vents i.e. small cracks usually appearing at the corners of cut glass, pits or digs i.e. small hollows and other defects.

While the glass is generally described herein as a sheet of glass, which may be flat or curved, it is to be understood that in many instances the glass is in the form of a laminated or tempered glass or other glass, to give it strength, shatter resistance or other properties. The processes used to form such glass may add to the potential defects in the sheet of glass.

Figure 3:
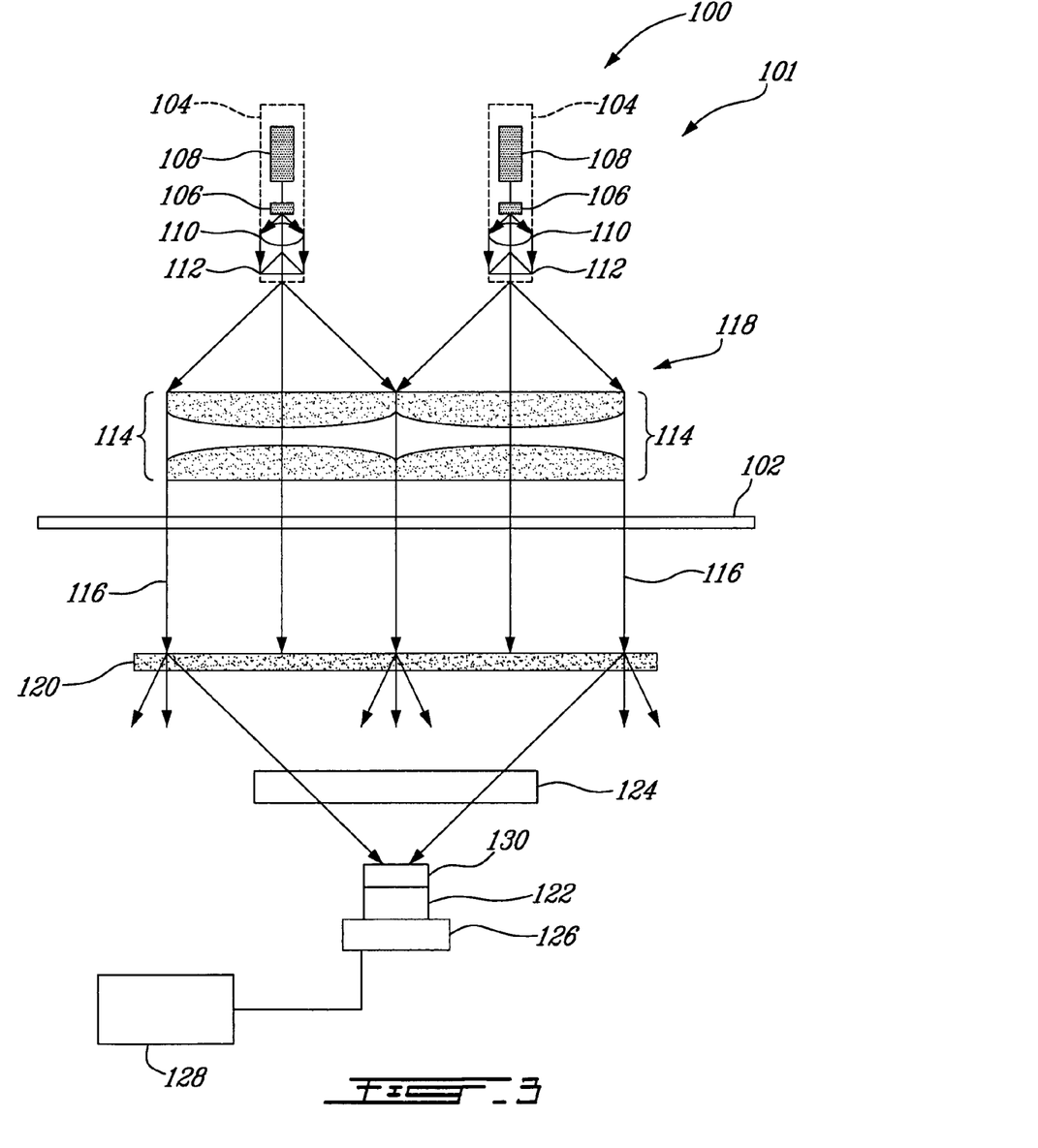
FIG. 3 is a schematic view of a Transmissive Bright Field channel of a glass inspection system in accordance with an embodiment of the present invention.

FIG. 3 schematically illustrates an automotive Bright Field (BF) channel 100 for a glass inspection system 101 where a glass sample 102 moves with constant speed V0 normally to the plane of FIG. 3. In order to suppress "draw lines", two low coherence illumination modules 104 are used for illumination. Each illumination module 104 uses a monochromatic low coherence point light source 106 connected to the power control printed circuit board (PCB) 108, a collimating lens 110 that creates parallel beams of light and a line generator 112 that transforms parallel beams of light into a divergent sheet of light. Aspheric lenses may be used as collimating lens 110. Line generators 112 may be of the type that creates a uniform light distribution along the generated line. Line generators 112 with such properties are manufactured by Stocker & Yale (Salem, N.H., USA). Visible range superluminescent diodes (SLED) may be used as the low coherence light sources 106. Adequate red light SLEDs are manufactured by Superlum Inc. (Moscow, Russia) and Inject (Saratov, Russia). The size of the SLEDs light emitter is similar to that of single mode semiconductor lasers, used in prior art. However, the coherence length of a typical red SLED is approximately 20-30 μm, which is smaller than a typical automotive glass thickness (2-5 mm) and much smaller than the coherence length of a typical single mode semiconductor laser diode. Because the coherence length of the light source 106 is much smaller than the thickness of the inspected glass sample 102, draw lines formation is prevented in the light images transmitted. Although multimode semiconductor lasers may be used as low coherence light sources it may be preferable not to do so as the size of their emitter is usually larger than that of SLEDs or single mode laser diodes, which creates certain light collimating problems.

The BF channel 100 uses a collimating lens system 118. A person skilled in the art would readily know that different lens combinations may be used for collimating light. For example, the collimating lens system 118 could be made, amongst others, of one or more cylindrical lens, one or more Fresnel lens, spherical or aspherical lenses or other known means of collimating light. Often, a tradeoff has to be made, especially with larger lenses, between optical quality and cost. For example, in the present embodiment, the collimating lens system 118 represented in FIG. 3 uses two pairs of cylindrical lenses 114. This is a collimating lens system often used in existing glass inspection systems because of its low cost. However, it has an inherent blind spot where defect may not be detected. Each illumination module 104 is installed in the respective focal points of the each pair of cylindrical lenses. Consequently, divergent sheets of low coherent light, generated by the illumination modules 104, which are installed in the respective focal point of each pair of cylindrical lens 114, are converted into parallel collimated sheets of light 116 by each pair of cylindrical lenses 114. BF collimated sheets of light 116 pass through the glass sample 102, which is moving along a production conveyor.

The light, passed through the glass sample 102 is received by a telecentric imaging lens system, which consists of a field lens 120 and of an objective lens 122 of BF camera 126. The distance between the field lens 120 and the objective lens 122 is equal to the sum of effective focal distances of these two lenses. The telecentric imaging lens system creates an image of the inspected glass in an image plane of the BF camera 126. The objective lens 122 may either use a fixed focal distance or be equipped with a zoom.

Different types of spherical/aspherical lenses, including inexpensive Fresnel lenses, may be used as field lens 120. The result of using a telecentric imaging lens system in the present embodiment is that a Point Spread Function (PSF) width of the BF channel 100 of the present embodiment is approximately half that of the BF channel of the glass inspection system 10 of the prior art as depicted in FIG. 1. Consequently, the detection capability of small and low optical density defects is substantially improved in the present embodiment.

To decrease the glass inspection system dimensions and to prevent broken glass from dropping onto the expensive objective lens 122, the BF light exiting the field lens 120 may be routed through a fold mirror 124. A BF line-scan camera 126, preferably being of the Time Delay Integration (TDI) type, is attached to the objective lens 122, and this assembly is focused on the inspected glass sample 102. The BF camera 126 may further be equipped with an antiblooming device, especially when inspecting dark glass samples 102. In the absence of defect, glass paintwork or ground edge, a photosensitive element of the BF camera 126 is illuminated. Any significant departure from a stationary illumination level is analyzed by an image acquisition/processing system 128 that is connected to the BF camera 126. Based on this analysis, the BF channel 100 generates a BF defect map for the inspected glass sample 102.

To facilitate the time delay integration effect of the BF camera 126, the glass conveying speed V0 has to be constant. The integration time of the BF camera 126, $\tau$, has to be calculated according to the formula:

$$\tau = \frac{P}{M \times V_0}$$

where P is the pixel size of the BF camera 126 and M is the optical magnification.

If the conveying speed of the glass sample 102 is not constant or if the integration time of the BF camera 126 is not correct, images obtained with the BF camera 126 will be blurred.

In order to inspect dark tinted glass samples 102, which may have a transmissivity down to 5%, at conveyor speed up to 800 mm/sec, it is necessary to either have more light reaching the BF camera 126 or to increase the camera sensitivity, or both. By comparison with prior art, removing the semitransparent screen 26 increases the light throughput by approximately 100 times. Typically, TDI line-scan cameras have approximately 30 to 50 times better sensitivity than single line line-scan cameras, such as those used in the prior art. By having more light reaching the BF camera 126 and by increasing the camera sensitivity, it is now possible to inspect dark tinted glass samples 102 at high conveying speed.

Another advantage of the TDI line-scan cameras over standard line-scan cameras, as used in prior art, is the fact that the TDI camera internally averages multiple subsequent images of a same inspected glass area. This averaging decreases the influence of a variation of local light intensity from the light source 106 on the image quality of the BF channel 100.

The inspection of dark tinted glass samples poses another problem: light intensity, passed through the glass sample 102 should be within the dynamic range of the BF camera 126 otherwise defect detection/classification algorithms, based on glass image processing, will fail. Consequently, the intensity of the light passing nearby the dark tinted glass sample 102 towards the BF camera 126 will significantly exceed the allowed dynamic range for the BF camera 126. For example, assuming that the glass sample 102 has a 5% transmissivity, this difference in light intensity may reach 20 times. In order to prevent image corruption due to a well known phenomenon called "blooming", antiblooming Charge Couple Device (CCD)-based or Complimentary Metal-Oxide-Semiconductor (CMOS)-based BF cameras 126 should be used. Antiblooming, TDI CCD-based line-scan cameras are manufactured, for example, by DALSA (Waterloo, ON Canada).

When this BF channel 100 is used in combination with an edge inspection module, it is necessary to protect the BF camera 126 from unwanted light penetration from the edge inspection module. In this case, an interference filter, such as a narrow bandpass filter 130 is attached to the objective lens 122. The filter 130 is capable to suppress, by either absorbing or reflecting back) most (approximately 99.99%) of the light emitted by the edge inspection module, which is scattered by the edges of the glass sample 102 towards the BF camera 126. Simultaneously, the filter 130 allows passing most of the light (approximately 65 to 70%) originating from the illumination modules 104 and reaching the BF camera 126. The spectral transmission characteristic of the filter 130 is selected so as to provide a maximum light throughput for the light coming from the illumination modules 104. Conversely, the light source of the edge module is selected so that the filter 130 may effectively suppress it.

This embodiment of the transmissive BF channel 100 may be installed a common compartment with a transmissive dark field (DF) channel, known in the prior art. This embodiment resolves previously known problems with "draw lines", false "broken glass" alarms, edge modules light penetration into the BF camera and dark tinted glass inspection at high conveying speed. Moreover, it also improves the defect detection capability for small and low optical density defects. It may be used as an upgrade for existing flat automotive glass inspection systems using combined transmissive BF/DF channels.

Figure 4:
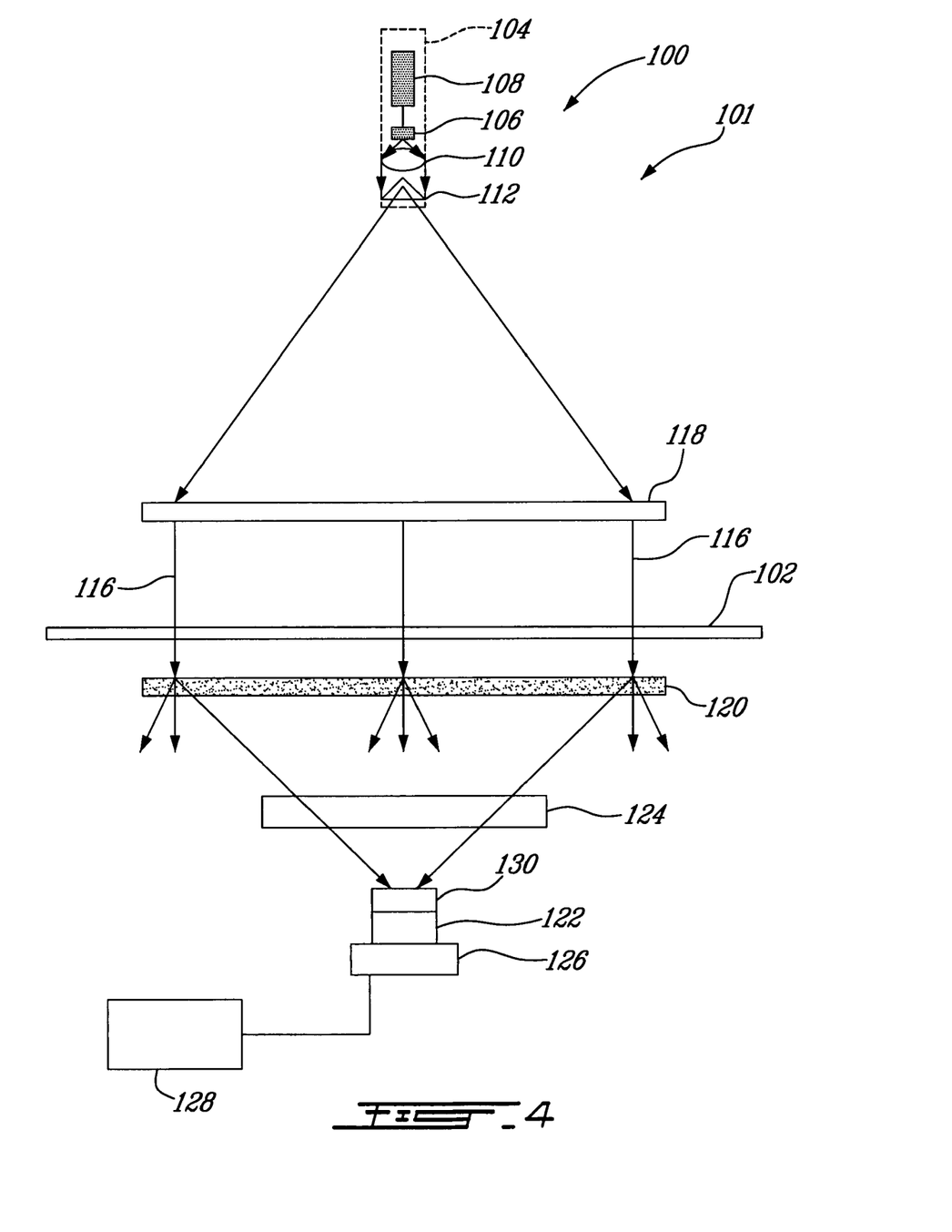
FIG. 4 is a schematic view of a Transmissive Bright Field channel of a glass inspection system in accordance with another embodiment of the present invention.

FIG. 4 illustrates a second embodiment for the BF channel 100 of the glass inspection system 101. In order to eliminate a well-known blind zone in the center of the field of view of some prior art transmissive BF channels, only one low coherence illumination module 104 is used for illumination. The illumination module 104 is installed at the focal point of the collimating lens 118. In the present embodiment, the collimating lens 118 may use, for example, one or more large cylindrical lens converting a divergent sheet of light, generated by the line generator 112, into a well-collimated sheet of light 116. The width of the collimated sheet of light 116 exceeds the one of prior art BF illuminator by a factor of two times or more. Typically, the width of the collimated light sheet 116 exceeds 450 mm.

In a particular case, the collimating lens system 118 consists of a single cylindrical (linear) Fresnel lens. An advantage of large size Fresnel lenses is that they are inexpensive. However, due to the relatively low optical quality of Fresnel lenses, such collimating lens system 118 cannot be used for DF illumination the same way it was done in the prior art. In the present case, a DF channel would have to be installed separately if required.

High quality cylindrical glass lenses may also be used for the collimating lens system 118. The advantage is that a BF and DF channel may then be combined and share the same collimating lens system 118 as it was done in the prior art. The drawback is that high quality glass lenses with a width 450 mm and more are expensive.

This second embodiment inherits all of the positive features of the first embodiment while, additionally, eliminating the well-know blind zone in the center of the field of view. It allows the inspection of flat and large sag (up to 400 mm) curved automotive glass such as sidelights, backlights and windshields.

In order to inspect wide automotive glass specimens, several BF channels 100, built in correspondence with this embodiment, may be used by having overlapping zones between the BF channels 100.

It is known in the art that light scattering on defects that are smaller than the light wavelength significantly depends on the light wavelength. Hence, it is preferable to use a light having a short wavelength since the intensity of the scattered light increases as approximately $\lambda$-4, where $\lambda$ is the light wavelength (Raleigh scattering). Scuff, or abrasion, and most of scratches are essentially glass surface defects with micro-irregularities inside a defective area. The stronger is the light scattering by these micro-irregularities, the more pronounced are drops of intensity for BF images associated with these defects.

According to our best knowledge, currently commercially available incoherent point light sources like Superluminescent Light Emitting Diode (SLEDs) and semiconductor multimode lasers emit light only in infrared (IR) and red regions of the spectrum. For improved scuff and scratch detection it would be advantageous to use blue and near ultraviolet (NUV) light sources. Automotive glass products are still transparent for blue and NUV regions of the light spectrum.

Figure 5:
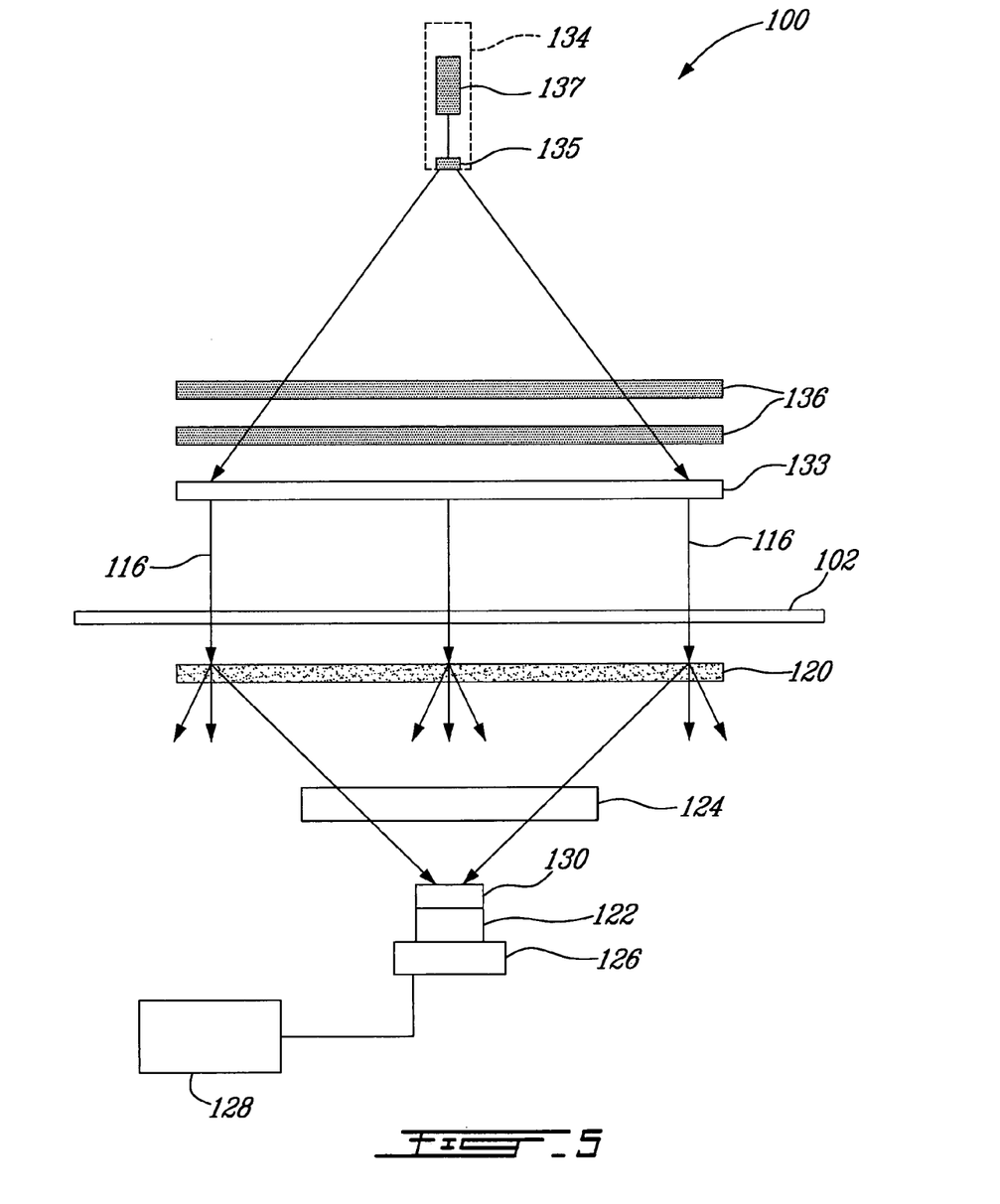
FIG. 5 is a schematic view of a Transmissive Bright Field channel of a glass inspection system in accordance with yet another embodiment of the present invention.

FIG. 5 illustrates another embodiment of the BF channel 100 for the automotive glass inspection system 101. In order to improve scratch and scuff detection, a short wavelength low coherence (SWLC) illumination module 134 is implemented. The SWLC illumination module 134 is installed at a focal point of a collimator 133, which, contrarily to the collimating lens system 118 of the previous embodiment, now uses spherical/aspherical lenses.

The SWCL illumination module 134 comprises a low coherence light source 135 connected to a power control PCB 137.

As opposed to the illumination module of the previous embodiments, the SWCL illumination module 134 does comprise neither the collimating lens 110 nor the line generator 112. The throughput improvement of the BF light, achieved through the use of the TDI line-scan camera 126 and through the omission of the semitransparent screen 26, is sufficient to do without these components in the present embodiment.

The collimator 133 converts the divergent beams of light generated by the SWCL illumination module 134 into the collimated sheet of light 116. The width of the collimated sheet of light is similar to the width of the one of the second embodiment. Typically, the width of the collimated sheet of light beam 116 equals or exceeds 450 mm.

In a particular case the collimator 133 consists of a single blue/NUV transparent spherical/aspherical Fresnel lens. Due to the relatively low optical quality of Fresnel lenses, such collimator cannot be used for dark field illumination in the same way it was used in the prior art. In the present case, a dark field channel would have to be installed separately if required. Although not having a high optical quality, Fresnel lenses are rather inexpensive.

High quality spherical/aspherical glass lenses may be used for the collimator 133, although such high quality glass lenses with a diameter of 450 mm and above are presently expensive.

Powerful short wavelength light emitting diodes LEDs should preferably be used as the low coherence light source 135. Such powerful LEDs are inexpensive. They allow a fast light modulation in the range or approximately 1 µsec. Powerful NUV LEDs ($\lambda$=365 nm, P≈200 mW) are manufactured, for example, by Nichia Corp. (Tokyo, Japan). Note that the automotive glass products are still transparent to NUV radiation having a wavelength $\lambda$ of 365 nm.

Halogen bulbs or like using small incandescent filaments may also be used as the low coherence light source 135. In this case, the installation of the narrow bandpass filter 130 is mandatory. However, a relatively short halogen bulb lifetime and problems with controlling light intensity create certain inconveniences with their implementation as the low coherence light source 135. Furthermore, it may be preferable that the low coherence light source 135 be monochromatic so as to avoid an image degradation caused by an inevitable chromatic aberration of the objective lens 122.

The size of a typical powerful LED emitter is approximately 1.0×1.0 mm to 1.5×1.5 mm. It is 200-300 times larger than the emitter size of a single mode semiconductor laser or of a SLED. Using such powerful LEDs as the light source creates certain collimation problems. As it follows from optical principles, the larger is the emitter size, the larger is the emitter radiation fan angle and the larger is the divergence angle for a collimated beam of a predefined collimated beam size. For paraxial optics, this principle is described by the Lagrange-Helmholtz invariant, which states that $\alpha \times d$ is a constant, where a is a beam divergence angle (in radians) and d is a beam diameter, no matter which optical components are used for paraxial beam transformation (excluding beam vignetting).

The distance between the glass sample 102 and the field lens 120 is significantly decreased (by approximately 6 times) in comparison with the same distance in prior art. For example, this distance is approximately 80 mm in the present embodiment versus 400-500 mm in the prior art. As a result, the image of a defect that is formed in the image plane of BF camera 126 is not significantly blurred, even though the divergence of the collimated sheet of light 116 may be larger than in the prior art.

It is possible that light, either from the illumination modules 104 or from ambient light, be reflected from a top or a bottom of an enclosure in which the BF channel 100 is placed. This may affect the performance of the glass inspection system. In order to suppress such light reflections, spatial filters 136 are installed. These spatial filters allow only a narrow strip of light, originating at the SWLC illumination module 134 to pass towards the collimator 133.

The BF channel 100 of the present embodiment may be used as an inexpensive BF channel for the inspection of both flat and small sag curved automotive glass. This BF channel 100 improves the detection level of scratched and scuffed glass.

Figure 6:
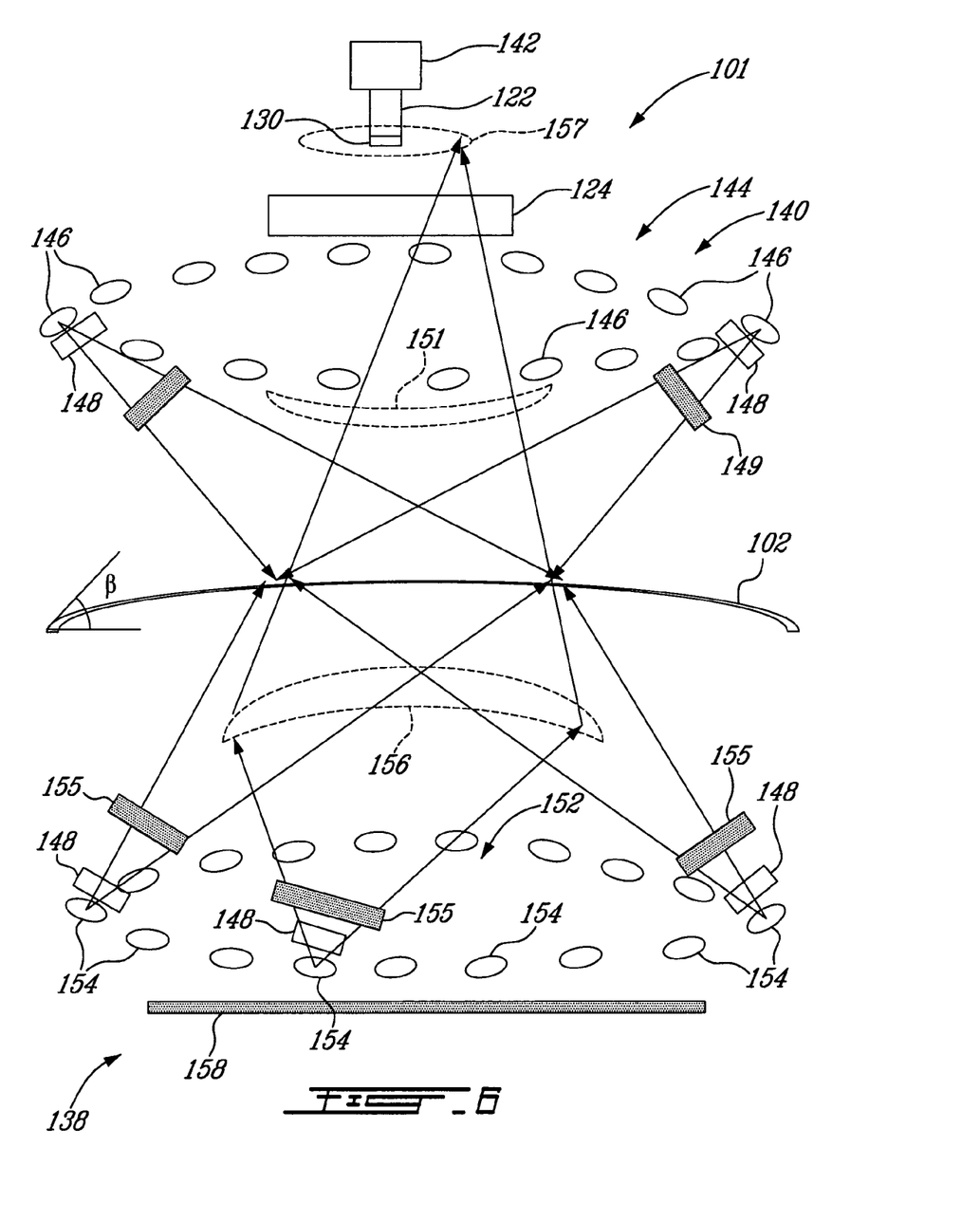
FIG. 6 is a schematic view of combined Transmissive Dark Field/Reflective Dark Field channels of a glass inspection system in accordance with another embodiment of the present invention.

Turning now to FIG. 6, there is depicted a glass inspection system 101 optionally combining a transmissive DF (TDF) channel 138 and a reflective DF (RDF) channel 140.

In order to create "360° all around" illumination for every point in a field of view 150 of a TDF/RDF camera 142 (best shown in FIG. 7, now concurrently referred to), two sets of light sources are installed. With respect to the glass sample 102, a set of Reflective Dark Field (RDF) light sources 144 is installed on the same side as the TDF/RDF camera 142. The set of RDF light sources 144 is installed to peripherally surround the field of view 150 of the TDF/RDF camera 142. In a particular example, the set of RDF light sources 144 may be installed to describe an ellipse or a circle around the field of view 150. Powerful LEDs, halogen bulbs, or the like may be used as RDF light sources 146 of the set of RDF light sources 144.

Figure 7:
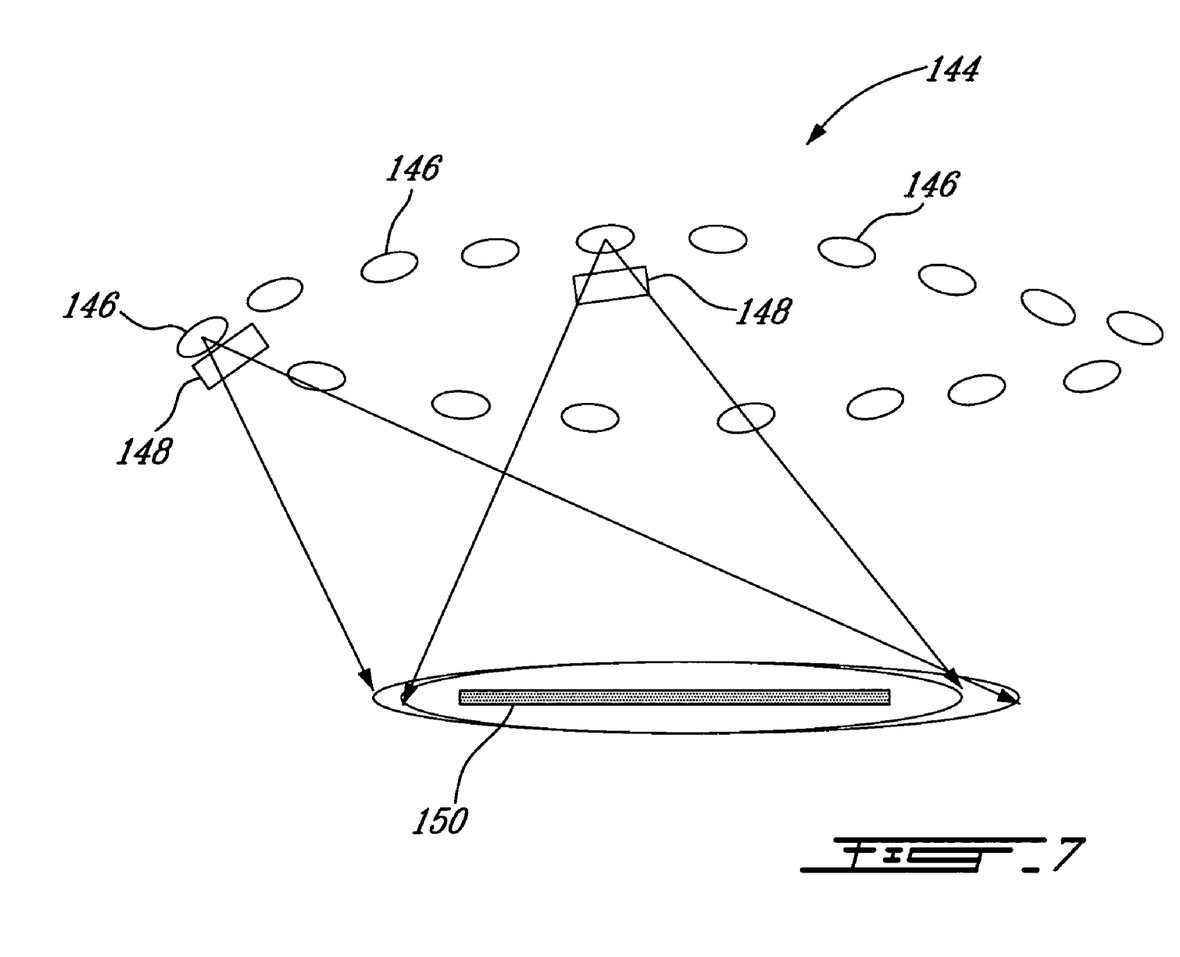
FIG. 7 is a partial schematic view of the combined Transmissive Dark Field/Reflective Dark Field channels of the glass inspection system of FIG. 6.

Optional beam shaping optical elements 148 may be installed between each light source 146 and the glass sample 102 (only some optical elements 148 are shown for the sake of clarity). Optical elements 148 may be aligned so that they redirect as much light from the RDF light sources 146 as possible to the field of view 150. Insofar as the field of view 150 of the line-scan TDF/RDF camera 142 is essentially a strip, a transmitted light pattern of the optical elements 148 may not be uniform. As a particular case, lenses with an elliptical transmitted light pattern may be used as the optical elements 148.

Long ellipse axes should be oriented along the field of view 150, as shown in FIG. 7. Such lenses, compatible with powerful LEDs, are manufactured, for example, by L2 Optics (Knaresborough, UK). Light behind the optical elements 148 is still divergent and directional.

The light emitted by the set of RDF light sources 144 is further scattered by one or more RDF anisotropic diffusive screens 149. Although the RDF anisotropic diffusive screens 149 are schematically depicted in FIG. 6 as each being dedicated to a single RDF light source, this is solely for the sake of simplicity and helping with understanding of the system. In real applications, there might be one or many RDF anisotropic diffusive screens 149 and each one may be associated to one, many or all RDF light sources 146. There may be either one large RDF anisotropic diffusive screen 149 or a plurality of smaller RDF anisotropic diffusive screens 149 adjacent one or more RDF light sources 146. For example, the RDF anisotropic diffusive screens 149 may take an elliptical or circular shape in order to match the shape of the set of RDF light sources 144. Divergent light beams from the adjacent RDF light sources 146 should significantly overlap each other on the surface of the RDF anisotropic diffusive screen 149. The distance between the RDF light sources 146 and the RDF anisotropic diffusive screen 149 is selected so as to provide this overlap. Consequently, the surface of the RDF anisotropic diffusive screen 149 acts as a continuous peripheral secondary divergent light source. This continuous peripheral secondary divergent light source provides a uniform "360° all around" RDF illumination for every point in the field of view 150 of the TDF/RDF camera 142. To increase the light throughput of the RDF anisotropic diffusive screen 149, a diffuser scattering fan angle should be small and perpendicular to the peripheral secondary divergent light source.

The RDF light sources 146, the optical elements 148 and the RDF anisotropic diffusive screen 149 should be aligned so that light beams reflected by the surface of the curved glass sample 102 would not reach the TDF/RDF camera 142. Actual positions of RDF light sources 146, of optical elements 148 and of the RDF anisotropic diffusive screen 149 depend on a maximum angle β between an object plane of the TDF/RDF camera 142 and the surface of the curved glass sample 102. The object plane is a plane that is perpendicular to an optical axe of the glass inspection system 101 and onto which the objective lens 122 is focused.

If the glass sample 102 does not show any scattering or diffractive defects on its surface, photosensitive elements of the TDF/RDF camera 142 do not receive any light. Conversely, if defects are present on the surface of the glass sample 102, light will be scattered or diffracted by the defects and will reach the TDF/RDF camera 146, thereby creating images of outbursts of light intensity on a dark background.

Optional field lens 151 may be installed between the glass sample 102 and the TDF/RDF camera 142 in order to increase the intensity of the scattered or diffracted light that reaches the TDF/RDF camera 142. In a particular case, the field lens 151 may create a telecentric pair with the objective lens 122 of the TDF/RDF camera 142. Furthermore, an optional fold mirror 124 may be installed to route the scattered/diffracted light towards the TDF/RDF camera 142.

Diffractive or scattering defects located on the upper surface of the glass sample 102, both in the "clear glass" area (the area where there is no paintwork) and in the area above paintwork, may be detected with the present RDF technique. If the glass sample 102 has a large coefficient of light transmission (~80-92%), the present RDF technique also allows the detection of diffractive/scattering defects on its lower surface, within the clear glass area. Because the coefficient of light transmission is not 100%, the scattered/diffracted light for such defects is not as intense as for similar defects on the upper surface.

If the glass sample 102 has a low coefficient of light transmission, a second set of light sources 152 has to be installed on the lower side of the glass sample 102, opposed the TDF/RDF camera 142. TDF light sources 154 are also installed in an elliptical or circular disposition around the field of view 150 of the TDF/RDF camera 142 and create a Transmissive Dark Field illumination. Powerful LEDs, halogen bulbs or the like may be used as the TDF light sources 154. In a particular case, the TDF light sources 154 may be identical to RDF light sources 146. The quantity of TDF light sources 154 may be different from the quantity of RDF light sources 146.

Optional beam shaping optical elements 148 may be installed between each TDF light source 154 and the glass sample 102. Optical elements 148 are aligned in such a way so as to redirect as much light from the TDF light sources 154 as possible towards the field of view of the TDF/RDF camera 142. Light beyond the optical elements 148 is divergent and directional.

Light coming from the TDF light sources 154 is further scattered by one or more TDF anisotropic diffusive screens 155. Divergent light beams from adjacent TDF light sources 154 should significantly overlap each other on the surface of the TDF anisotropic diffusive screens 155. The distance between TDF light sources 154 and the TDF anisotropic diffusive screens 155 is selected so as to provide this overlap. As a result, a continuous ellipse or ring of virtual secondary divergent light sources is created on the surface of the one or more TDF anisotropic diffusive screens 155. This continuous ellipse or ring of secondary divergent light sources provides a uniform "360° all around" TDF illumination for every point within the field of view 150 of the TDF/RDF camera 142. Similarly with the RDF anisotropic diffusive screens 149, the TDF anisotropic diffusive screens 155, may take, for example, an elliptical or circular shape allowing it to match the shape of the set of TDF light sources 152. There may be either one large TDF anisotropic diffusive screen 155 or a plurality of smaller TDF anisotropic diffusive screens 155 adjacent one or more TDF light sources 154.

It is also important that the TDF light sources 154, the optical elements 148 and the TDF anisotropic diffusive screen 155 be positioned and aligned such that light beams coming for the TDF light sources 146 and passing through the glass sample 102 do not directly reach the TDF/RDF camera 142.

An optional spherical/aspherical collimating lens 156 may be installed between the TDF anisotropic diffusive screen 155 and the glass sample 102, preferably such that the TDF anisotropic diffusive screen 155 is positioned in its focal plane. The spherical/aspherical collimating lens 156 focuses light beams passing through the TDF anisotropic diffusive screen 155 into a peripheral shape 157 (for example, elliptical or circular ring) having a dark area in its center. The objective lens 122 of the TDF/RDF camera 142 is positioned within this dark area. This allows decreasing an angle between the optical axis of the objective lens 122 and light beams generated by the TDF light sources 154 without exposing the TDF/RDF camera 142 to these light beams. In turn, it improves the detection of diffractive/scattering defects, especially those defects having a narrow scattering/diffractive diagram.

The spherical/aspherical collimating lens 156 requires an antireflective coating on its surfaces and has to be positioned at a significant distance from the glass sample 102 in order to exclude reflection of RDF light beams from its surfaces to the TDF/RDF camera 142.

Only defects that scatter, diffract or significantly refract light, such as scuff, scratches or cold glass, are likely to be detected by the present TDF technique. Defects which just absorb light and have low scattering boundaries, such as all kinds of thin films on the glass surface, are likely not to be detected by the present TDF technique.

When this glass inspection system 101 is used in combination with an edge inspection module, it may be necessary to protect the TDF/RDF camera 142 from unwanted light penetration from the edge inspection module. As with other inspection system described, it is possible to use an interference filter, such as the narrow bandpass filter 130 attached to the objective lens 122.

To exclude parasitic reflections into the TDF/RDF camera 142, a light beam absorber 158 may be installed opposed to the TDF/RDF camera 142, covering its whole field of view 150.

Figure 8:
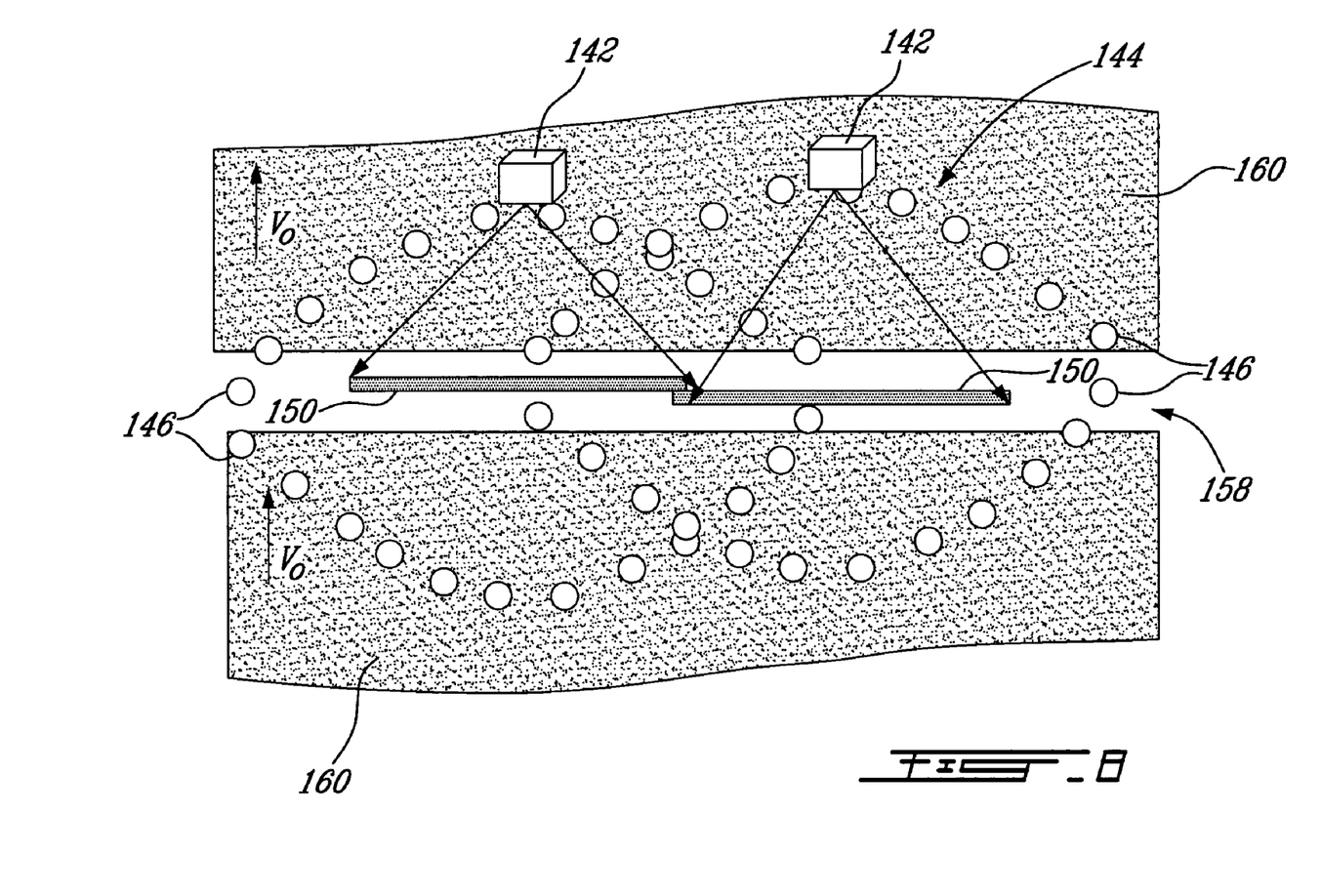
FIG. 8 is a schematic top view of an arrangement on an inspection line using two glass inspection systems of FIG. 6.

In order to inspect wide automotive glass samples, several RDF/TDF channels 138, 140, built in correspondence with the present embodiment, may be assembled by having overlapping zones between the channels, as depicted in FIG. 8.

Some automotive glass manufacturers safely transport curved glass products using wide belt conveyors. A gap between the wide belt conveyors is required so that the RDF/TDF channels of an inspection system perform adequately. It would be advantageous that all the fields of view of all RDF/TDF cameras be within the same gap.

FIG. 8 depicts a top view of a multi-channel RDF/TDF inspection system, installed inside a single gap 158 between wide belt conveyors 160. The set of RDF light sources 144 is installed on the same side of the glass sample as the TDF/RDF camera 142. The set of RDF light sources 144 is installed in the elliptical or circular disposition around the field of view of the TDF/RDF camera 142. RDF light sources 146 create Reflective Dark Field illumination. In order to overlap the fields of view 150 of multiple TDF/RDF cameras 142 within the same gap 158, the set of RDF light sources 144 should be arranged side by side, a bit staggered as is shown in FIG. 8. The sets of TDF light sources 152 (not shown) may be arranged in a similar manner.

It will be apparent to those skilled in the art that various modifications and variations can be made to the BF and DF channels for glass inspection systems of the present invention without departing from the spirit or scope of the invention. Thus, it is intended that the present invention covers the modifications and variations of this invention provided they come within the scope of the appended claims and their equivalents.

I claim:

1. An inspection system for inspecting a sheet of glass comprising:
    an illumination module having a low coherence light source emitting light;
    a collimating lens system having a focal point on the main axis thereof and producing a collimated sheet of light from said emitted light for passing through the sheet of glass, said light source being located at said focal point;
    a telecentric imaging lens system for concentrating said sheet of light passed through the sheet of glass on an image formation plane; and
    a Time Delay Integration line-scan camera positioned in a general area of said image formation plane, said camera being equipped with an antiblooming device.

2. The inspection system of claim 1 wherein said telecentric imaging lens system further comprises a field lens and an objective lens.

3. The inspection system of claim 2 further comprising a narrow bandpass filter located between said field lens and said objective lens of said telecentric imaging lens system so as to completely close an aperture of said camera.

4. The inspection system of claim 3 wherein said illumination module comprises a collimating lens and a line generator.

5. The inspection system of claim 4 wherein said light source is a SLED.

6. The inspection system of claim 5 wherein said light source produces a short wavelength light.

7. The inspection system of claim 4 further comprising a plurality of illumination modules and wherein said collimating lens system comprises a corresponding plurality of pairs of cylindrical lenses, each said illumination modules being associated with one of said pairs of cylindrical lenses.

8. The inspection system of claim 3 further comprising a spatial filter located between said illumination module and said collimating lens system, said collimating lens system comprising a collimator.

9. The inspection system of claim 8 wherein said collimating lens system comprises at least one lens selected from the group consisting of spherical lens and aspherical lens.

10. The inspection system of claim 9 wherein said light source is a LED.

11. The inspection system of claim 10 wherein said light source produces a short wavelength light.

12. An inspection system for inspecting a sheet of glass having a first side and a second side, the inspection system comprising:

a camera having a field of view, said camera being positioned on and pointing toward the first side of the sheet of glass; and a substantially elliptical peripheral RDF illumination module, said RDF illumination module surrounding said camera and being located on the first side and outside said field of view, said RDF illumination module being operative to illuminate said field of view with its RDF emitted light, said RDF illumination module being oriented so that the sheet of glass reflects said RDF emitted light away from said camera, wherein said camera is positioned so as to be operative to receive said RDF emitted light if a RDF detectable defect is present on the sheet of glass and to avoid said RDF emitted light if no RDF detectable defect is present on the sheet of glass.

13. The inspection system of claim 12 further comprising:

a peripheral TDF illumination module, said TDF illumination module surrounding said camera and being located on the second side and outside said field of view, said TDF illumination module being operative to illuminate said field of view with its TDF emitted light, wherein said camera is positioned so as to be operative to receive said TDF emitted light if a TDF detectable defect is present in the sheet of glass and to avoid said TDF emitted light if no TDF detectable defect is present in the sheet of glass;

a collimating lens system positioned between said TDF illuminating module and the sheet of glass, said collimating lens system having a focal plane, said collimating lens system being operative to direct said TDF emitted light away from said camera, said TDF illumination module being placed substantially within said focal plane; and a field lens positioned between the sheet of glass and said camera.

14. The inspection system of claim 13 further comprising a light beam absorber installed opposed to said camera and covering said field of view, said light beam absorber being operative to exclude parasitic reflections from reaching into said camera.

15. The inspection system of claim 14 further comprising a plurality of beam shaping optical elements adjacent said plurality of light sources of each of said RDF and TDF illumination modules, said plurality of beam shaping optical elements being operative to redirect light emitted from said plurality of light sources towards said field of view of said camera, said inspection system further comprising a plurality of anisotropic diffusive screens adjacent said plurality of beam shaping optical elements.

16. The inspection system of claim 15 wherein each of said RDF and TDF illumination modules comprises a plurality of light sources.

17. The inspection system of claim 16 wherein each of said RDF and TDF illumination modules emits monochromatic light having substantially the same wavelength.

18. The inspection system of claim 17 wherein said camera is equipped with a narrow bandpass filter and wherein said camera is a line-scan, Time Delay Integration camera comprising an antiblooming device.

19. The inspection system of claim 18 further comprising a field lens installed between the sheet of glass and said camera and creating a telecentric pair with an objective lens of said camera, said field lens being operative to concentrate light scattered or diffracted by defects in the sheet of glass.

20. The inspection system of claim 12 wherein said peripheral TDF illumination module has a substantially elliptical shape.

* * * * *